United States Patent [19]

Kozischek

[11] 4,147,766

[45] Apr. 3, 1979

[54] MACROSPHERICAL PARTICLES OF ANTI-PERSPIRANTS

[75] Inventor: James F. Kozischek, Belvidere, N.J.

[73] Assignee: Armour Pharmaceutical Company, Phoenix, Ariz.

[21] Appl. No.: 694,419

[22] Filed: Jun. 9, 1976

[51] Int. Cl.$^2$ ............................ F26B 3/08; F26B 7/00; F26B 19/00; C07F 7/00; C07F 5/06; C01B 7/00; A61J 3/07; A61K 7/38

[52] U.S. Cl. .......................................... 424/14; 34/10; 34/12; 34/60; 260/429.3; 260/448 R; 423/462; 424/46; 424/66; 424/68

[58] Field of Search ................. 424/66, 68, 14; 34/12, 34/10

[56] References Cited

U.S. PATENT DOCUMENTS

| | | | |
|---|---|---|---|
| 3,014,844 | 12/1961 | Thiel et al. | 424/46 |
| 3,516,941 | 6/1970 | Matson | 252/522 X |
| 3,619,842 | 11/1971 | Maierson | 252/316 |
| 3,679,102 | 7/1972 | Charle et al. | 424/47 X |
| 3,691,271 | 9/1972 | Charle et al. | 424/47 X |
| 3,791,987 | 2/1974 | Fanger | 424/65 UX |

Primary Examiner—Dale R. Ore
Attorney, Agent, or Firm—Richard R. Mybeck; William W. Schwarze

[57] ABSTRACT

A process and apparatus are provided for making hollow macrospherical particles. The particles themselves are particularly adapted for use as anti-perspirants. The particles have a diameter between about 10 and 74 microns, preferably predominating between 15 and 44 microns, and a greater than unit density. As such, they are not subject to deep lung penetration. The process for producing the particles comprises providing a solution containing the materials from which the particles are made, diffusing the solution through small pores by centrifugal force such that the resulting hollow particles have a diameter greater than the pore diameter, and drying the solution droplets in a stream of heated air. The apparatus for producing the macrospherical particles comprises a centrifugal atomizer having a porous sintered metal filter ring which is rotated inside a spray drying chamber. The filter is treated to produce hollow macrospheres having substantially smooth outer walls of such thickness that they can withstand normal shipment and handling without significant fragmentation.

6 Claims, 3 Drawing Figures

MACROSPHERICAL PARTICLES OF ANTI-PERSPIRANTS

BACKGROUND OF THE INVENTION

This invention pertains to hollow, thick walled macrospherical particles intended for use primarily as anti-perspirants. The macrospherical particles may also be used in pigments, resins, catalysts, etc.

For the last ten or fifteen years, aerosol sprays have been a major application form for many products such as hair spray, paint, anti-perspirant powders, and countless others. For the purposes of this application, "aerosol" means a suspension of fine solid particles in a gas. The gas need not be halohydrocarbon gases such as Freon which have been widely used as propellants, but may include air or any other gaseous propellant.

In a recent article, Cambridge, G. W., "Inhalation Toxicity Studies", *Aerosol Age*, May 1973, 32, the author focused on the current public and regulatory awareness to pulmonary deposition and possible retention of inhaled aerosol products. The study pointed out that, while penetration into and deposition in the respiratory tract is influenced to some extent by the frequency and depth of breathing, the major factor is the size and shape of the particle representing inhaled particulate matter. The nose, as the primary filter, retains virtually all particles in excess of 10 microns in diameter. Approximately 50% of 5 micron particles are retained, while almost all 1-2 micron particles penetrate beyond the nose. Particles below 5 microns are respirable and will penetrate into the lung if the particles are of unit or lower density.

Hatch, T. F. and Gross, P., *Pulmonary Deposition and Retention of Inhaled Aerosols*, Academic Press, N.Y., 1964, define aerodynamic particle size as "the diameter of a unit density sphere having the same settling velocity as a particle in question of whatever shape and density". These authors have shown that the degree of respiratory penetration and retention is a direct function of the aerodynamic particle size. In effect, the denser a particle, the less respirable it is, even at particle diameters less than 10 microns, if the density is a high order of magnitude.

Sciarra, J. J., McGinley, P., and Izzo, L., "Determination of Particle Size Distribution of Selected Aerosol Cosmetics. I. Hair Sprays", *J. Soc. Cosm. Chem.* 20, 385-394, May 27, 1969, reported that while most particles below 50 microns will remain suspended in air for relatively long periods of time, only those particles less than 10 microns are likely to pass into the respiratory tract. Most of the particles of this size will be retained in the upper portions of the respiratory tract, while particles in the range 2-5 microns may be deposited in the area of terminal bronchi and alveoli.

Thus, it is apparent that certain particles suspended in an aerosol may be harmful to the respiratory system. In view of this, the present invention was developed. The particles of the present invention are hollow macrospherical particles having a size predominantly between about 10 and 74 microns, and preferably between about 15 and 44 microns, in diameter and having a density greater than 1. These particles are of a large enough size and density to be substantially filtered out by the nose and to avoid deep respiratory tract penetration and deposition.

Prior art particles have either been so small that they have been respired and retained in the lungs, or have been so large that the various valves, dip tubes and orifices of aerosol sprayers become clogged due to agglomeration in the very small openings through which the compositions must pass. This tendency to agglomeration has made it necessary to grind or mill the particles prior to its formulation as a suspension, but even with such prior treatment, agglomeration has continued to be a problem.

It has recently been reported in *Drug & Cosmetic Industry*, September, 1975, p. 132, that some companies "are attempting to sidestep the problem of zirconium inhalation by reformulating their aerosol anti-perspirants to limit spray particles to more than 10 microns, a feat aerosol veterans say may be especially difficult because of shearing and break-up in the upper valve and in the actuator."

Gilman U.S. Pat. No. 3,887,692, issued to the assignee of the present application, discloses basic aluminum halides in microspherical form and aerosol anti-perspirant compositions containing them, as well as processes for preparing the halides in microspherical form. Such microspheres, while uniformly spheroidal in shape, are solid, and thus require more material to make them.

The microspheres disclosed in U.S. Pat. No. 3,887,692 are made by a process in which an aqueous solution of the basic aluminum halides is discharged through a hollow tube or needle in a fine stream against the side of a vortex of whirling organic alcohol. As the vortex whirls, the very fine droplets of the halide assume spherical form. They are then separated from the alcohol and incorporated in an aerosol anti-perspirant composition.

There are several centrifugal particle forming and drying processes and apparatus known in the prior art. See, for example, U.S. Pat. Nos. 1,352,623, 2,043,378, and 3,259,171. The last-mentioned patent discloses a slinger for forming particles to be spray dried. The slinger comprises a screen having a multiplicity of openings through which clay is extruded by centrifugal force, which is used as feed stock. While the patent discloses that the particles are of substantially the same size and shape, they are not hollow nor are they spherical. The particles produced do not have a diameter substantially larger than the openings in the screen.

The above-mentioned patents also disclose apparatus for producing particles by centrifugal force. None, however, teach the use of a porous sintered metal filter capable of producing hollow macrospherical particles in accordance with the present invention.

U.S. Pat. No. 2,829,710 discloses an atomizing dryer but of a substantially different structure than that of the present invention.

Beeco Products Company sells a series of spray head atomizers designated as BEECOMIST spray heads. These devices use controlled-porosity sintered-metal sleeves for spraying fluids, usually liquid solutions for the control of agricultural pests and diseases using droplets from 10 to 1000 microns in diameter. The BEECOMIST spray heads are generally mounted on crop dusting aircraft or carried on farm land vehicles, rather than being placed in a spray drying apparatus.

Conventional spray dryers use an atomizer which is simply a spinning plate which has the liquid solution fed in streams to the underside of the plate. The liquid is spun off the plate by centrifugal force resulting in the formation of liquid droplets which are then dried in mid-air by a hot air stream. See Bulletin 33-3 of Bowen Engineering, Inc., North Branch, N.J. for a description of a conventional spray drying system. Another conventional spray drying apparatus comprises a drilled hole atomizer which includes a cylindrical or basket-like structure for receiving the solution and drilled holes of about 3/16 inch diameter, for example, in the peripheral walls to allow jets of solution to escape into the drying chamber. Both of these conventional methods rely essentially on hydrodynamic centrifugal atomization by the Rayleigh jet break-up phenomenon. Such conventional systems do not produce macrospherical particles such as those disclosed in the present application.

SUMMARY OF THE INVENTION

Hollow macrospherical particles to be used in an aerosol are produced which have diameters predominantly between about 10 and 74 microns, and preferably between 15 and 44 microns, with a density greater than unit density. The particles have sufficient wall thickness to withstand the usual treatment to which they are subject in shipping and handling without substantial fragmentation into smaller particles which may become respired and retained in the lungs.

The process for producing the hollow macrospherical particles comprises providing a solution containing the materials from which the particles are made, diffusing the solution through small pores by centrifugal force such that the diameter of the particles is larger than the nominal diameter of the pores, and drying the solution in a stream of heated air after it leaves the pores. Approximately 85% of the particles diffused through the pores have diameters of between about 15 and 74 microns.

The apparatus for producing the dry, hollow macrospherical particles comprises a centrifugal atomizer having a filter ring made of porous sintered metal of substantially uniform pore size which is mounted in a spray drying chamber. The outer surface of the porous sintered metal filter is ground or polished and etched to provide a smooth surface with sharp pore exits to produce hollow, thick-walled macrospheres having a diameter larger than the diameter of the pores.

At this point, it is important to define the term "macrospherical particles" as used herein and to distinguish these from the microspherical particles of the prior art. A. M. Rubino, "'Microspherical Powder' aerosol antiperspirant systems", *Aerosol Age*, Vol. 19, No. 5, pages 21-25 (May 1974) describes microspherical antiperspirants which comprise hollow spherical particles confined to a relatively narrow range, namely 70% or more of the particles having diameters between about 15 and 44 microns with virtually no particles larger than 45 microns diameter and particles smaller than 5 to 10 microns being minimized. This microspherical particle size distribution is obtained by mechanical classification of the particles after spray drying. The particles have an apparent density of about 0.8 gm/ml.

Although the macrospherical particles of the present invention also have a size distribution concentrated in the 15-44 micron range, there are a number of important differences. First of all, at least about 85 percent of the particles are greater than 15 microns in diameter with few greater than 74 microns, which means that only about 10-15 percent at the maximum are fines (below 15 microns) and only a few percent are below 10 microns. This contrasts to the 15-30 percent fines in the microspherical grade. Secondly, the macrospherical grade of the present invention is formed directly by spray drying without a subsequent mechanical classification to remove larger particles. Thirdly, the macrospherical particles are relatively thick walled and have a true density greater than 1.0, and typically have an apparent or bulk density about twice as great as the microspherical grade. This latter characteristic was quite unexpected and is advantageous because of the greater "apparent size" according to the unit density theory of Hatch and Gross, supra.

It will be understood by those skilled in the art that particle size measurements will vary depending upon the particular method of measurement. Accordingly, unless otherwise indicated, all particle sizes referred to herein are obtained by a wet sieving method.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE PREFERRED EMBODIMENTS

Figure 1:
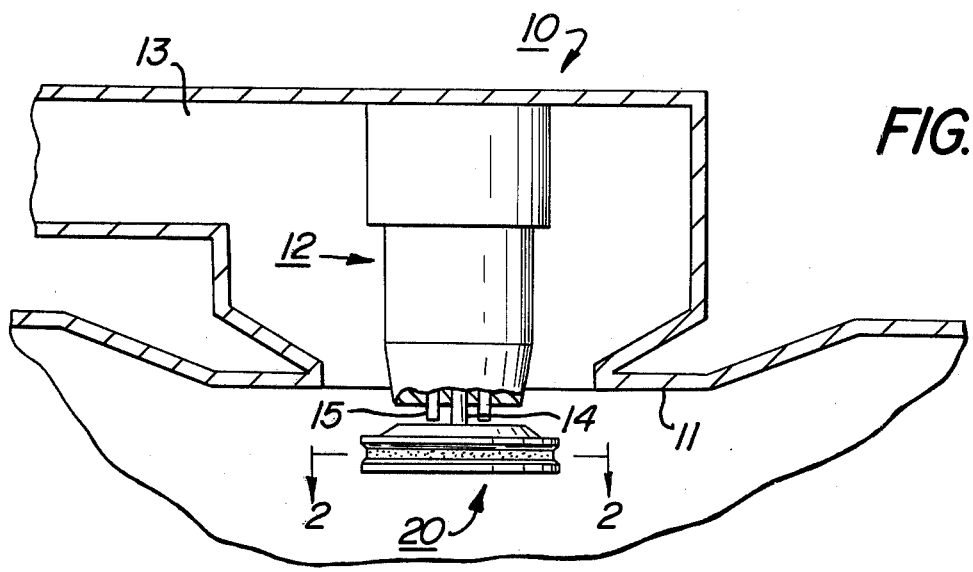
FIG. 1 is a partial side elevational view of the atomizer according to the present invention as it is mounted in the center of the top wall of the spray drying chamber.

Referring to the drawings in detail, wherein like numerals indicate like elements, there is shown in FIG. 1 a spray drying apparatus 10 constructed in accordance with the present invention. For a description of a conventional spray drying system and an illustration of the spray drying chamber used in connection with the preferred embodiment of the present invention, see Bulletin 33-3 of Bowen Engineering, Inc.

Spray drying apparatus 10 comprises spray drying chamber (not completely shown), having a top wall 11, in the center of which is mounted atomizer drive motor 12. The spray drying chamber is shaped generally like an inverted, substantially conical housing having restricted air path 13 immediately above the atomizer 20. The atomizer 20 is connected by motor drive shaft 14 to the motor. Port 15 is provided for the introduction into the atomizer of a solution of the material from which the particles are made.

Figure 2:
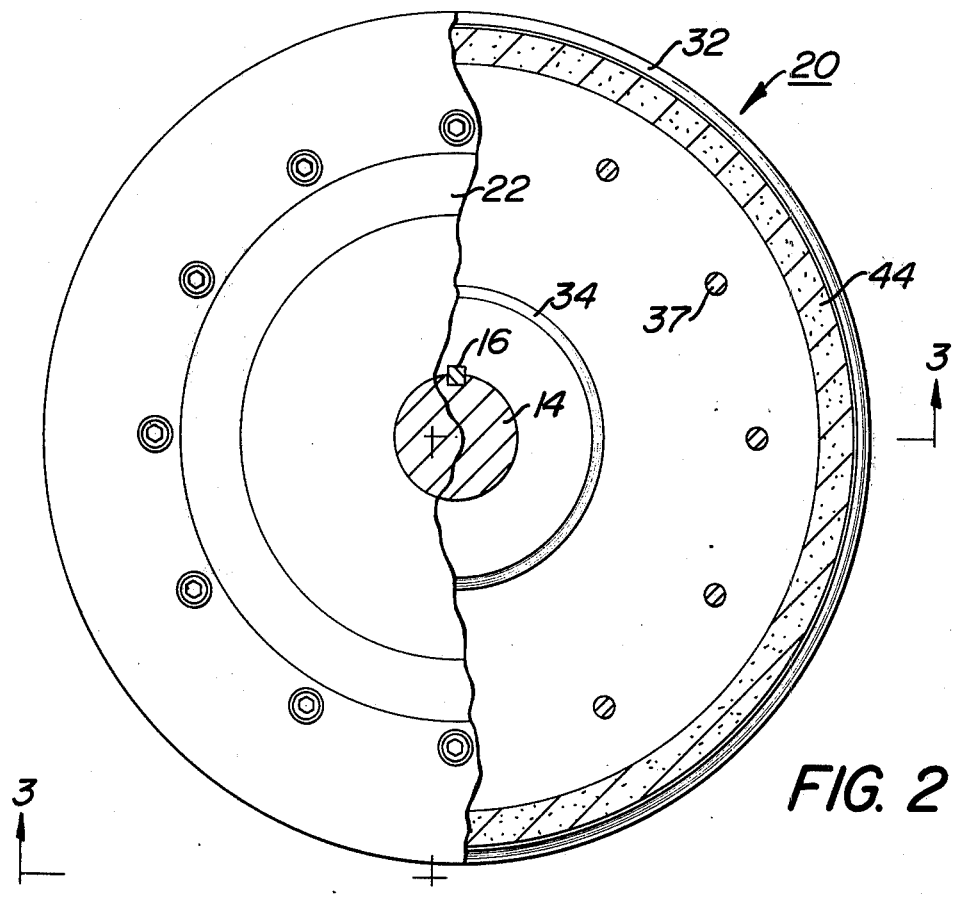
FIG. 2 is a plan view of the atomizer, taken partly in section along line 2—2 of FIG. 1.
Figure 3:
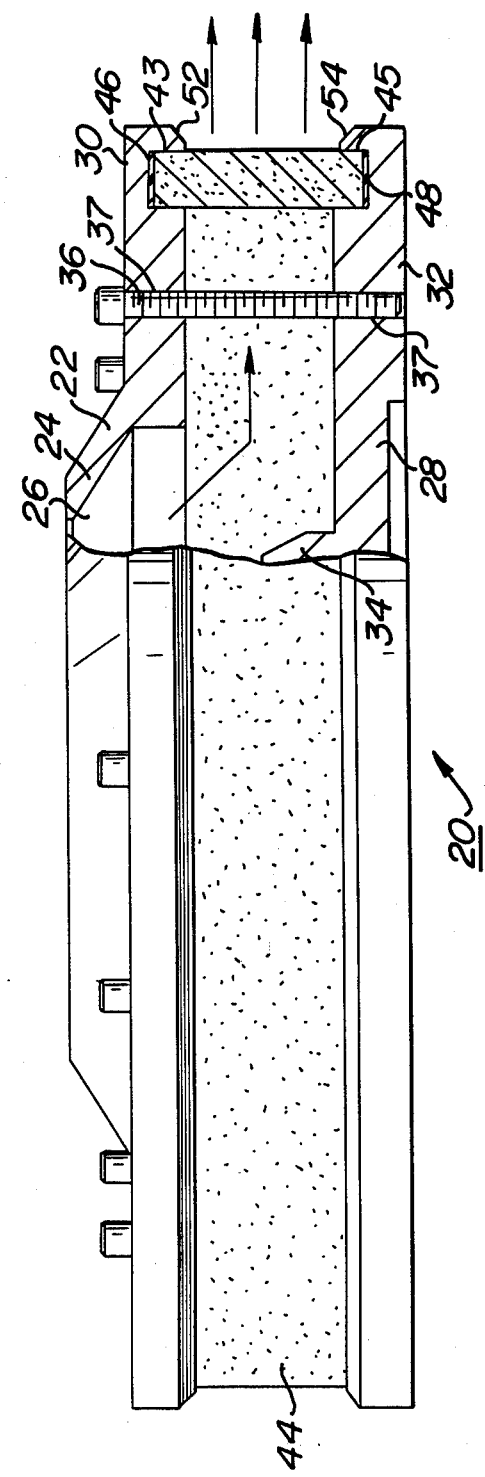
FIG. 3 is a side elevation view of the atomizer taken partly in section along line 3—3 in FIG. 2.

The atomizer itself is shown more clearly in FIGS. 2 and 3. Atomizer 20 comprises a circular top member 22 having a truncated conical portion 24 defining an inlet 26 through which the solution is introduced into the atomizer. Top member 22 is connected by a plurality of screws 36 passing through screw holes 37 to circular bottom member 28.

Bottom member 28 has a raised central portion 34 to which drive motor shaft 14 is attached by any suitable means. For example, a lower portion of drive shaft 14 may extend below bottom plate 28. This lower portion may be threaded and nuts and lock nuts may be applied to retain the atomizer on the drive shaft. Drive shaft 14 has an anti-slip key portion 16 attached thereto to prevent relative spinning of the shaft and atomizer.

Top member 22 and bottom member 28 have annular flange portions 30 and 32, respectively. Recess 43 is formed in flange portion 30 and recess 45 is formed in flange portion 32. The recesses are in vertical alignment with each other. Cylindrical filter 44 is disposed between top member 22 and bottom member 28 within recesses 43 and 45, respectively. Appropriate sealing means 46 and 48, for example, Teflon tape seals the space between filter 44 and top member 22 and bottom member 28.

Filter 44 is a porous tubular member capable of withstanding high rotational speeds without breaking apart. Because of the high peripheral speeds involved, about 1500 to 6000, and preferably about 2100 to 5100 inches per second, standard ceramic porous tubes are not particularly useful in the present invention.

In view of the high speeds involved, the filter is preferably made from porous sintered metal, such as Monel metal or 316 stainless steel. To produce particles having a narrow size distribution, that is, between about 10 and 74 microns in diameter, and preferably between about 15 and 44 microns in diameter, a tube having a high degree of uniform porosity is required. Porous sintered metal tubes made by some known processes frequently have areas of greater and lesser density. These tubes are not preferred in the present invention, since they may produce significant amounts of particles having diameters less than about 10 microns in diameter which are respirable and capable of deep lung penetration.

Filters which are particularly useful in the present invention are the porous sintered metal filters manufactured, for example, in accordance with the teachings of U.S. Pat. Nos. 2,792,302 and 3,313,621. Filters of this type are manufactured, for example, by Mott Metallurgical Corporation of Farmington, Conn. Other methods of making porous sintered metal elements having uniform porosity are disclosed, for example, in U.S. Pat. Nos. 2,157,596, 2,398,719, 3,052,967 and 3,700,419. Uniform porosity can be enhanced by using spherical powdered metal particles for sintering and forming filter ring 44.

The thickness of filter ring 44 is not critical so long as it is thick enough so that it will not break apart at the higher rotational speeds to which it is subjected in use. A thickness of ⅜ inch has been found to be useful. Likewise, the height of filter 44 is not critical. The height should be a function of the feed rate of the liquid solution from which the hollow microspherical particles are produced. A suitable feed rate is 0.5-2.5 lb/min/inch$^2$ of the inner surface of the filter ring. It can be seen that the effective height of the filter as well as its circumference are factors which determine the allowable feed rate of the liquid. "Effective height" is defined as the height of filter 44 between the inner surfaces of top member 22 and bottom member 28. Of course, the full height of filter 44 must be more than the effective height so that it can be retained in recesses 43 and 45. A feed rate of about 1.2 lb/min/inch$^2$ is preferred when using a filter ring 44 having an effective height of 1 inch and having a diameter of 8 inches.

To be most effective, it is preferred that the outer surface of filter 44 be ground and then chemically etched to give a sharp edge to the exit orifice of each of the pores. The pores having sharpened edges will chop off the stream of liquid to give particles having a more uniform size than if the surface were not so treated. Typically, the outer surface of the porous metal ring is first machined to the appropriate dimension and then ground smooth by any appropriate technique. The grinding results in sharpening the exit orifices of the pores in the porous filter. However, the machining and grinding cause some of the pore exits to become partially or totally blocked by flowed metal. Therefore, it is necessary to reactivate or unblock the pores by a controlled etching step. Many chemical etching solutions are known which may be used for this purpose, depending upon the particular metal chosen for the filter and other factors which will be recognized by those skilled in the art.

The nominal pore size of the pores in filter 44 may be from about 15 to 30 microns in diameter. If the nominal pore size is smaller than this, the pores tends to clog and the particles may be respirable. If the pore size is much more than 30 microns, the particles produced are too large and too coarse, tending to agglomerate and stick on the sides of the drying chamber. A nominal pore size of 20 microns is presently preferred. The term "nominal pore size" is used to mean the intended size of the vast majority of pores. Thus, with a filter having a nominal pore size of 20 microns, almost all of the pores will have this size but invariably, some will be larger and some will be smaller.

A filter having a nominal pore size of 20 microns will produce particles having an average or nominal size of about 30 microns in diameter. The dried macrospherical particles are larger in size than the nominal pore size of the filter because through some unknown phenomenon the dried particles blow up or balloon as they become hollow. The walls of the hollow macrospherical particles also increase in thickness during this process. Again, the exact reasons are unknown to applicant.

The end portions of annular flanges 30 and 32 of top member 22 and bottom member 28 respectively are angled, as at 52 and 54, best seen in FIG. 3. By angling these inside end portions at approximately 45°, accumulation of particles on the inner surfaces of flange portions 30 and 32 and the outside of filter ring 44 is either eliminated or greatly reduced. Top member 22 and bottom member 28 may be made of any material such as stainless steel which can withstand the high speeds at which the atomizer is rotated and which can withstand any corrosive tendencies of the liquids from which the macrospherical particles are produced.

The operation of the atomizer will now be described. First, the spray drying apparatus is turned on. Then, as the atomizer begins to spin at peripheral speeds of from about 2100 to about 5100 inches per second, solution from which the microspherical particles are made are fed into atomizer 20 through inlet 26 from solution feed port 15. The feed rate is adjusted so that the solution diffuses promptly through filter ring 44. Thus, the feed rate is adjusted so that there is very little, if any, solution build-up within the atomizer. The flow of the solution through inlet 26, toward filter 44 and out of the atomizer into the air currents of the spray drying apparatus is shown by arrows in FIG. 3. Because of the rapid spinning of the atomizer, the uniformly small pores of the filter ring, and the treatment of the exterior surface of the filter ring, the stream of liquid diffusing through filter 44 is cut-off into tiny droplets. As the droplets are propelled from the atomizer into the air currents of the spray dryer, they dry and expand into hollow, thick-walled macrospherical particles. The spray dryer dries the droplets by evaporating water from them with a stream of heated air, although other gases could be used, having an inlet temperature, for example, of from about 450° to about 540° F. and an outlet temperature, for example, of about 195° to about 250° F. The liquid stream should be a clear solution, as distinguished from an emulsion, a suspension or a mixture, to prevent blinding of the filter pores.

The resulting macrospherical particles are dry, hollow and have thick walls. The walls are thick enough so that the macrospherical particles can withstand the treatments usually encountered during shipping, handling and dispensing. The hollow particles have a greater than unit true density and typically have an apparent or bulk density as great as about twice the normal density obtained from conventional spray drying. This factor is important in that very small particles which may otherwise be respirable settle very quickly when sprayed into the air. This counteracts the tendency to inhale the particles. Thus, not only are the particles generally large enough so that deep lung penetration is avoided, but also the smaller particles, theoretically capable of being respired deeply into the lungs, settle quickly when sprayed into the air. Particles having a size less than about 15 microns in diameter are agglomerated by oils and other ingredients in the final product but, if not, the greater than unit density particles have an effective size of greater than 15 microns in diameter for purposes of respiration kinetics. The macrospherical particles of the present invention have a substantially smooth exterior surface.

The particles are thoroughly dried in the spray dryer, the operating conditions required depending on the particular constituents of the solution from which the particles are made, but readily determinable by those skilled in the art of spray drying. Since hygroscopicity is a big factor in anti-perspirant materials, the particles should be overdried (to the extent possible without affecting antiperspirant properties), that is, dried beyond their capacity in a meta stable state so as to have a very high affinity for water. Since the human breathing tract has 100% relative humidity, there is high agglomeration of the smaller particles which minimizes the chances of the particles less than 15 microns in diameter actually deeply penetrating into the lungs.

After the desired quantity of spray-dried material has been produced and collected, the dryer is shut down. Using the method and apparatus of the present invention, the walls of the drying chamber generally have at most a light coating of dried, macrospherical particles. As compared to the prior art spray drying techniques, this is a distinct advantage, as the prior art devices and processes using similar operating conditions frequently result in the walls of the drying chamber being covered with a heavy, wet coating of the product being dried. Thus, according to the present invention, the amount of usable material which can be recovered from the spray drying chamber is greatly increased. Quite obviously, the operating conditions using prior art devices and processes can be varied to reduce or eliminate chamber build-up, but only at the expense of particle size, i.e., the particles produced will be too small to fall within the desired range for avoiding inhalation and deep lung penetration.

Although the macrospherical particles produced by the process and apparatus of the present invention may have many areas of use, such as pigments, resins, catalysts, etc., the preferred use is to produce particles of anti-perspirant material. Since anti-perspirants have wide public use, it is important that the particle size be so controlled so as to reduce health hazards as much as possible. The present invention causes the particle size to fall predominantly within a narrow range of safety and effectiveness, namely between about 10 and 74 microns, and preferably between about 15 and 44 microns in diameter.

The solution from which the hollow, thick walled macrospherical particles of anti-perspirant material are produced may be selected from any of a wide variety of known anti-perspirant ingredients, including but not limited to: basic aluminum compounds, basic aluminum-zirconium complexes, basic aluminum-magnesium complexes, basic aluminum-polyol complexes, magnesium-zirconium complexes and mixtures thereof. Although particular compounds within the broad classes just described are known to those skilled in the anti-perspirant manufacturing art, the following more specific compositions are examples of the above-named classes of compounds.

The basic aluminum halides are examples of basic aluminum compounds suitable for use in the present invention. A representative formula is:

$$Al_n(OH)_xA_y \cdot XH_2O$$

wherein x and y need not be integers but $x+y=3n$, X is a quantity from 2 to 4 which need not be an integer, and A is chlorine, bromine, iodine or mixtures thereof. Compounds within this general formula include the 5/6 basic aluminum halides which have the formula $[Al_2(OH)_5A]$ and the $\frac{2}{3}$ basic halides $[Al(OH)_2A]$. For convenience, brackets are used to enclose groups of chemical elements which are not necessarily all of the elements of the molecular structure, and do not mean to exclude $H_2O$ groups.

A widely used anti-perspirant complex is aluminum chlorhydroxide or 5/6 basic aluminum chloride which is commercially available from Reheis Chemical Company division of Armour Pharmaceutical Company under the trademark "CHLORHYDROL". Many other anti-perspirant materials and additives useful in the present invention will be apparent to those of ordinary skill in the art.

The above compounds may be used in an aqueous solution which is delivered to the atomizer. The aqueous solution contains sufficient water or other diluent to enable it to diffuse through the atomizer pores. Typically, a 50% by weight aqueous solution of the compounds has been found satisfactory, but if still lower viscosity is desired, the solution may be heated or may be diluted with water or alcohol to, for example, 25% by weight of the compound in the solution. As pointed out above, the solution should be a true solution so as to avoid blinding the pores of the filter.

It is beneficial at this point to review, briefly, those factors which affect particle size distribution of spinning-disc type atomizers. Reference is made, therefore, to "Atomization and Spray Drying" by W. R. Marshall, Jr. (Chemical Engineering Process Monograph Series Vol. 50, No. 2, 1954, American Institute of Chemical Engineers, New York, New York). In Chapter VIII, "Drop-Size Distribution from Spinning Disc Atomizers", the author reviews the work of various researchers in this field and shows that for a wide variety of spinning disc atomizers operated over a wide variety of conditions, drop-size distribution (and quite obviously dry particle size distribution) is a function solely of feed rate, atomizer diameter and rotational speed. These latter two factors combined give peripheral speed. (See the above-cited reference, particularly pages 68–71 and FIGS. 98 and 100–102.)

For an atomizer to produce particles of a size and range not conforming to those produced by a conventional spinning disc atomizer at the same peripheral speed and feed rate, it would have to be concluded that its atomizing mechanism differed from that of the conventional type. Although applicant does not wish to be bound by any particular theory, it is believed that atomization according to the present invention may properly be characterized as "mechanical", as opposed to the "hydrodynamic" atomization obtained by conventional centrifugal atomization. That is, whereas conventional atomization relies solely, or at least predominantly, on centrifugal force and the Rayleigh jet break-up phenomenon, atomization according to the present invention appears to occur by a mechanical chopping off of droplets from the solution stream. Thus, using the centrifugal force generated by the rotating atomizer of the present invention, the feed solution is forced against the interior wall of the cylindrical porous metal filter, where it is then extruded through the pores of the filter in the form of fine "rods" of liquid. The sharp edges of the pores "chop off" these rods as they emerge from the outer wall of the cylinder, after which the chopped off droplets reform into spheres by virtue of surface tension.

To demonstrate the difference between the particles produced by conventional centrifugal atomization and those produced using the apparatus and method of the present invention, several solutions were prepared and tested under similar conditions of peripheral speed and feed rate using a 30 inch diameter Bowen laboratory spray dryer. In each of the examples, the conventional centrifugal atomization used a spinning plate distributor, and the porous metal atomization used the apparatus and method of the present invention. The measurement and comparison of results between the conventional system and the system of the present invention will now be illustrated in more detail with reference to the following specific, non-limiting examples:

EXAMPLE I

Comparison Between Conventional Centrifugal Atomization and Porous Metal Atomization Spray Drying of a 50% Solution of 5/6 Basic Aluminum Chloride (Aluminum Chlorohydrate)

Into a 500-gallon reactor equipped with agitation and a heat exchanger was charged 2950 pounds of 24° Baume AlCl$_3$ and 1720 pounds of water. After preheating, 580 pounds of aluminum powder was added in 10 pound increments maintaining an average reaction temperature of about 85° C. After approximately 6 hours, when nearly all of the aluminum had dissolved, an additional 35 pounds of aluminum powder was added and the batch filtered. The aforesaid composition assayed 12.6% Al and 8.5% Cl. Two batches of the solution were spray dried as follows:

| | | Conventional Centrifugal | Porous Metal |
|---|---|---|---|
| 1) | Type Atomization | | |
| 2) | Run Conditions: | | |
| | A) Feed Rate, ml/min | 100 | 100 |
| | B) Total Wt. Feed, gm | 4,000 | 4,000 |
| | C) Run Duration, min. | 30 | 30 |
| | D) Inlet Temperature, °F. | 445 | 445 |
| | E) Outlet Temperature, °F. | 195 | 200 |
| | F) Atomizer Diameter | 2" | 1½" |
| | G) Atomizer Speed, RPM | 20,000 | 27,000 |
| | H) Atomizer Perif. Speed, in./sec | 2,094 | 2,120 |
| | I) Build-up in Chamber | Heavy | Light |
| 3) | Al in Feed Solution | 12.6 | 12.6 |
| 4) | % Al in Dry Powder | 25.6 | 26.0 |
| 5) | Theo. Yield Based on Al, gms. | 1,969 | 1,938 |
| 6) | Actual Yield (Cyclone Product), gm. | 821 | 1,699 |
| 7) | % Recovery (6) ÷ (5) × 100 | 41.7 | 87.7 |
| 8) | Wt. Chamber Build-up, gms. | 877 | Slight |
| 9) | Particle Size Distribution of Cyclone Product (By Wet Sieve): | | |
| | A)* % + 74 μ | 2.2 | 0.3 |
| | B) % + 44 μ | 25.2 | 12.9 |
| | C) % + 15 μ | 94.4 | 91.4 |

"+" means retained on sieves of the indicated size and those above it (i.e., cumulative distribution)

EXAMPLE II

Comparison Between Conventional Centrifugal Atomization and Porous Metal Atomization Spray Drying of a 42% Solution of Zirconium-Aluminum Chlorhydroxide-Glycine Complex To 2000 grams of basic aluminum chloride solution was added 840 grams of water. Dissolved in this mixture, at room temperature, was 190 grams of glycine, N.F. grade, using mild agitation. When all the glycine had dissolved, 1650 grams of zirconyl hydroxy chloride solution (14.2% Zr) at room temperature was added over a one-half hour period. The clear solution contained 6.2% Al. Two batches of solution were spray dried as follows:

| | | Conventional Centrifugal | Porous Metal |
|---|---|---|---|
| 1) | Type Atomization | | |
| 2) | Run Conditions: | | |
| | A) Feed Rate, ml/min | 100 | 100 |
| | B) Total Wt. Feed, gm | 4,000 | 4,000 |
| | C) Run Duration, min. | 29 | 28 |
| | D) Inlet Temperature, °F. | 540 | 540 |
| | E) Outlet Temperature, °F. | 230 | 230 |
| | F) Atomizer Diameter | 2" | 1½" |
| | G) Atomizer Speed, RPM | 20,000 | 27,000 |
| | H) Atomizer Perif. Speed, in/sec | 2,094 | 2,120 |
| | I) Build-up in Chamber | Heavy, Wet | Light |
| 3) | % Al in Feed Solution | 6.2 | 6.2 |
| 4) | % Al in Dry Powder | 14.4 | 14.7 |
| 5) | Theo. Yield Based on Al, gm | 1,722 | 1,687 |
| 6) | Actual Yield (Cyclone Product), gm | 453 | 1,387 |
| 7) | % Recovery (6) ÷ (5) × 100 | 26.3 | 82.2 |
| 8) | Wt. Chamber Build-up | Too Wet To Weigh | Slight |
| 9) | Particle Size Distribution of Cyclone Product (By Wet Sieve): | | |
| | A) % + 74 μ | 0.8 | 0.3 |
| | B) % + 44 μ | 24.7 | 7.8 |
| | C) % + 15 μ | 98.1 | 91.3 |

EXAMPLE III

Comparison Between Conventional Centrifugal Atomization and Porous Metal Atomization Spray Drying of a 33% Solution of Aluminum-Zirzonium Chlorhydroxide Complex To 2720 grams of water were added 2662 grams of basic aluminum chloride and heat to 90° C. while maintaining good agitation. When the solution had reached 90° C., 2070 grams of zirconyl hydroxy chloride solution (13.7% Zr) were added over a period of one hour. When the zirconyl hydroxy chloride addition was complete, the batch was refluxed (100°–105° C.) for one-half hour; then the batch was cooled to room temperature.

The clear solution assayed 5.8% aluminum. Two batches of the solution were spray dried as follows:

| | | Conventional Centrifugal | Porous Metal |
|---|---|---|---|
| 1) | Type Atomization | | |
| 2) | Run Conditions: | | |
| | A) Feed Rate, ml/min | 100 | 100 |
| | B) Total Wt. Feed, gm | 4,000 | 4,000 |
| | C) Run Duration, min. | 32 | 40 |
| | D) Inlet Temperature, °F. | 500 | 500 |
| | E) Outlet Temperature, °F. | 250 | 250 |
| | F) Atomizer Diameter | 2" | 1¼" |
| | G) Atomizer Speed, RPM | 20,000 | 27,000 |
| | H) Atomizer Perif. Speed, in/sec | 2,094 | 2,120 |
| | I) Build-up in Chamber | Heavy | Very Light |
| 3) | % Al in Feed Solution | 5.8 | 5.8 |
| 4) | % Al in Dry Powder | 17.4 | 18.0 |
| 5) | Theo. Yield Based on Al, gm | 1,333 | 1,259 |
| 6) | Actual Yield (Cyclone Product), gm | 227 | 906 |
| 7) | % Recovery (6) ÷ (5) × 100 | 17.0 | 70.3 |
| 8) | Wt. Chamber Build-up, gm | 509 | Slight |
| 9) | Particle Size Distribution of Cyclone Product (By Wet Sieve): | | |
| | A) % + 74 μ | 1.4 | 0.4 |
| | B) % + 44 μ | 26.9 | 5.2 |
| | C) % + 15 μ | 96.5 | 86.7 |

EXAMPLE IV

Comparison Between Conventional Centrifugal Atomization and Porous Metal Atomization Spray Drying of a 50% Solution of ⅝ Basic Aluminum Chloride-Glycine Complex To 2000 grams of 50% aqueous solution of basic aluminum chloride was added 1000 grams of 32° Baume aluminum chloride. This mixture was reacted by subjecting to reflux conditions (100°–105° C.) for a period of four hours. To the hot solution was added 140 grams of glycine, N.F. grade, which was allowed to dissolve completely. When all the glycine was dissolved, the solution was cooled to room temperature. The clear solution contained 10.1% aluminum. Two batches of the solution were spray dried as follows:

| | | Conventional Centrifugal | Porous Metal |
|---|---|---|---|
| 1) | Type Atomization | | |
| 2) | Run Conditions: | | |
| | A) Feed Rate, ml/min | 100 | 100 |
| | B) Total Wt. Feed, gm | 4,000 | 4,000 |
| | C) Run Duration, min. | 30 | 35 |
| | D) Inlet Temperature, °F. | 500 | 500 |
| | E) Outlet Temperature, °F. | 250 | 250 |
| | F) Atomizer Diameter | 2" | 1¼" |
| | G) Atomizer Speed, RPM | 20,000 | 27,000 |
| | H) Atomizer Perif. Speed, in/sec | 2,094 | 2,120 |
| | I) Build-up in Chamber | Heavy, Wet | Light |
| 3) | % Al in Feed Solution | 10.1 | 10.1 |
| 4) | % Al in Dry Powder | 20.9 | 21.5 |
| 5) | Theo. Yield Based on Al, gm | 1,933 | 1,879 |
| 6) | Actual Yield (Cyclone Product), gm | 566 | 1,359 |
| 7) | % Recovery (6) ÷ (5) × 100 | 29.3 | 72.3 |
| 8) | Wt. Chamber Build-up | Too Wet To Weigh | Slight |
| 9) | Particle Size Distribution of Cyclone Product (By Wet Sieve): | | |
| | A) % + 74 μ | 3.4 | 0.3 |
| | B) % + 44 μ | 32.3 | 28.2 |
| | C) % + 15 μ | 98.1 | 99.1 |

EXAMPLE V

Comparison Between Conventional Centrifugal Atomization and Porous Metal Atomization Spray Drying of a 40% Solution of Zirconium-Aluminum Chlorhydroxide-Glycine Complex In another example, the superior atomizing ability under constant conditions of peripheral speed and feed rate of the present apparatus over conventional spinning disc atomizers was shown. In this instance, the spray dryer was a 14-foot-diameter, cone bottom, co-current, commercial-sized unit Model MlAl manufactured by Bowen Engineering, Inc. The solution was prepared in the same manner as in Example II above, except that a larger batch was made.

| | | Conventional Centrifugal | Porous Metal |
|---|---|---|---|
| 1) | Type of Atomization | | |
| 2) | Atomizer | 8" diameter with 3/16" drilled holes | 8" diameter porous metal |
| 3) | Atomizer Speed, RPM | 12,400 | 12,400 |
| 4) | Atomizer Peripheral Speed, inches per second | 5,100 | 5,100 |
| 5) | Solution Feed Rate, pounds per minute | 30.0 | 29.9 |
| 6) | Particle Size Distribution of Product: | | |
| | % + 74 μ | 22.2 | 1.8 |
| | % + 44 μ | 49.7 | 15.7 |
| | % + 15 μ | 97.6 | 90.2 |
| | % + 10 μ | 98.6 | 93.6 |

Here again, a significant increase in the amount of particles produced in the size range between 15 and 74μ using the porous metal atomizer is clearly demonstrated. There was also a large product build-up on the dryer walls with the conventional atomization, but only a light build-up with the porous metal atomization. It is not to be inferred that the particle size distribution achieved with the conventional atomizer could not be improved by varying operating conditions. But it follows that further optimization of the end product from the porous metal atomizer could also be realized.

An analysis of the data contained in the above examples leads to the following conclusions:

(1) In all cases, the conventional centrifugal atomizer left a heavy (and wet) build-up of material in the drying chamber. This implies that a great preponderance of the feed solution was atomized into droplets too large to be dried before they struck the chamber wall and hence adhered to it. As a result, dried powder yields collected in the cyclone dryer varied from 17.0% to 41.7% (Examples I–IV).

In all cases, the porous metal atomizer left a very light chamber build-up, implying that the solution was adequately atomized for drying. As a result, dry powder yields collected in the cyclone dryer were 70.3% to 87.7% (Examples I–IV).

(2) In all cases, the porous metal atomizer produced a particle content of metal higher in aluminum and/or zirconium than the conventional centrifugal atomizer. This implies superior atomization for the porous metal atomizer since large or irregularly-shaped particles are more difficult to dry and hence, would tend to have a higher final moisture and therefore, a lower metal content.

(3) In all cases, the porous metal atomizer produced a substantially greater percentage of particles having diameters between 15 and 74 microns. The percentages varied from about 8 to 13 percent more particles within this size range than by using the the conventional centrifugal atomizer. Moreover, all of the material left on the chamber walls can be considered to comprise particles larger than 74 microns.

It can therefore be concluded that the porous metal atomizer produces a material with a substantially narrower particle size distribution than a conventional centrifugal atomizer and that the atomization mechanism is uniquely different.

Since in all cases, both the yield was higher and the particle size distribution was narrower for the porous metal atomizer than the conventional centrifugal atomizer, a greater amount of usable macrospherical particles result per unit of solution processed when using the porous metal atomizer.

No attempt was made in the above examples to optimize particle size distribution viz-a-viz a finished commercial product specification. The runs were intended only to show the differences between the two types of atomization. To as great an extent as possible, run conditions, such as feed rate, inlet temperature, outlet temperature, duration of run, etc., were kept constant to provide meaningful comparisons.

The examples demonstrate the quantitative advantages of the present invention. The qualitative advantages include hollow, thick-walled macrospherical particles with a greater apparent density and which are more able to withstand the destructive forces associated with processing, handling, shipping and dispensing. Thus, the increased resistance to fragmentation results in reduced amounts of particles below 10 microns in size.

The present invention may be embodied in other specific forms without departing from the spirit or essential attributes thereof and, accordingly, reference should be made to the appended claims, rather than to the foregoing specification as indicating the scope of the invention.

I claim:

1. Hollow, thick-walled macrospherical particles, said walls consisting essentially of anti-perspirant material, at least about 85 percent of said particles having diameters greater than 15 microns and few of said particles having diameters greater than 74 microns, said particles having a true density greater than 1, the walls of said particles having sufficient thickness to withstand shipping, handling and dispensing without substantial fragmentation into smaller particles which may be respired and retained in the lungs.

2. Macrospherical particles according to claim 1 wherein said anti-perspirant material includes basic aluminum compounds having the formula:

$$Al_n(OH)_xA_y.X\ H_2O,$$

wherein x and y need not be integers but x+y=3n, X is a quantity from 2 to 4 which need not be an integer, and A is selected from the group consisting of chlorine, bromine, iodine and mixtures thereof.

3. Macrospherical particles according to claim 1 wherein said anti-perspirant material comprises basic aluminum compounds selected from the group consisting of basic aluminum-zirconium complexes, basic aluminum-magnesium complexes, basic aluminum-polyol complexes and mixtures thereof.

4. Macrospherical particles according to claim 1 wherein said particles are magnesium-zirconium complexes.

5. Macrospherical particles according to claim 1 wherein said particles have substantially smooth exterior surfaces.

6. Macrospherical particles according to claim 1 wherein said particles have an average diameter of 30 microns.

* * * * *